United States Patent [19]

Reiners et al.

[11] Patent Number: 4,904,750

[45] Date of Patent: Feb. 27, 1990

[54] ESTER-URETHANE DERIVATIVES OF (METH)-ACRYLIC ACID FOR DENTAL MATERIALS

[75] Inventors: Jürgen Reiners, Leverkusen; Carlhans Süling, Odenthal; Walter Schäfer, Leichlingen; Hanns P. Müller, Bergisch-Gladbach; Wolfgang Podszun, Cologne; Jens Winkel, Cologne Pesch, all of Fed. Rep. of Germany

[73] Assignee: Bayer Aktiengesellschaft, Leverkusen, Fed. Rep. of Germany

[21] Appl. No.: 287,424

[22] Filed: Dec. 20, 1988

[30] Foreign Application Priority Data

Dec. 23, 1987 [DE] Fed. Rep. of Germany ....... 3743782

[51] Int. Cl.$^4$ ................................................ C08G 18/04
[52] U.S. Cl. ..................................... 526/301; 560/115; 560/158; 106/35; 433/228.1
[58] Field of Search ................ 526/301; 560/115, 158; 106/35; 433/228.1

[56] References Cited

U.S. PATENT DOCUMENTS 4,820,745  4/1989  Muller et al. ........................ 526/301

Primary Examiner—Maurice J. Welsh
Attorney, Agent, or Firm—Sprung Horn Kramer & Woods

[57] ABSTRACT

Dental fillings, coatings and teeth are formed of polymers and copolymers of a polyfunctional ester-urethane derivative of (meth)-acrylic acid of the formula

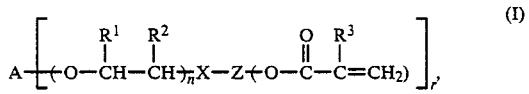

in which A is a straight-chain or branched aliphatic radical which has 2 to 20 carbon atoms and optionally contains 1 to 3 oxygen bridges, an aromatic radical with 6 to 24 carbon atoms, an araliphatic radical with 7 to 26 carbon atoms or a cycloaliphatic radical with 6 to 26 carbon atoms, r denotes the number of chains starting from A and denotes a number from 2 to 6, $R^1$ and $R^2$ are identical and denote hydrogen or are different and denote hydrogen and methyl, n denotes a number from 0 to 5 independently for each chain starting from A, X stands for the group

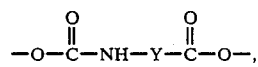

in which Y denotes a divalent (cyclo)aliphatic radical which has 2 to 15 carbon atoms and optionally contains ester, ether or urethane groups, Z denotes a divalent straight-chain or branched aliphatic hydrocarbon radical which has 3 to 15 carbon atoms and can optionally contain 1 to 3 oxygen bridges and can optionally be substituted by 1 to 4 additional (meth)-acrylate radicals and $R^3$ denotes hydrogen or methyl independently for each chain starting from A.

9 Claims, No Drawings

ESTER-URETHANE DERIVATIVES OF (METH)-ACRYLIC ACID FOR DENTAL MATERIALS the invention relates to new ester-urethane derivatives of (meth)-acrylic acid, their preparation and their use as monomeric components for dental materials.

The use of polyfunctional (meth)-acrylic acid derivatives as components for dental filling materials is known. Acrylic acid esters and meth-acrylic acid esters of pentaerythritol are thus described in EP-A 0,017,936. The monomers described therein give, in combination with inorganic fillers, dental materials which have an undesirable polymerization shrinkage which leads to the formation of fissures between the dental material and filling material.

(Meth)-acrylic acid derivatives containing urethane groups, for adhesives in the dental field, in which the urethane groups are substituted by a radical containing a (meth)-acrylate group are described in U.S. Pat. No. 4,554,336. As components in dental compositions, these compounds display inadequate properties, in particular a strength which is too low in practice.

New ester-urethane derivatives of (meth)-acrylic acid of the formula (I)

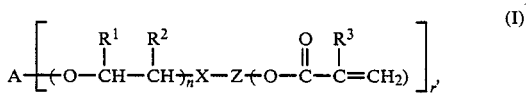

in which
A is a straight-chain or branched aliphatic radical which has 2 to 20 carbon atoms and optionally contains 1 to 3 oxygen bridges, an aromatic radical with 6 to 24 carbon atoms, an araliphatic radical with 7 to 26 carbon atoms or a cycloaliphatic radical with 6 to 26 carbon atoms,
r stands for the number of chains starting from A and denotes a number from 2 to 6,
$R^1$ and $R^2$ are identical and denote hydrogen or are different and denote hydrogen and methyl, n denotes a number from 0 to 5 independently for each chain starting from A,
X stands for the group

in which
Y denotes a divalent (cyclo)aliphatic radical which has 2 to 15 C atoms and optionally contains ester, ether or urethane groups,
Z denotes a divalent straight-chain or branched aliphatic hydrocarbon radical which has 3 to 15 carbon atoms and can optionally contain 1 to 3 oxygen bridges and can optionally be substituted by 1 to 4 additional (meth)-acrylate radicals and
$R^3$ denotes hydrogen or methyl independently for each chain starting from A,
have now been found.

Dental materials for which the ester-urethane derivatives, according to the invention, of (meth)-acrylic acid are used as starting substances surprisingly show a considerably low polymerization shrinkage, a relatively high abrasion resistance and a relatively high strength and are therefore particularly suitable for use in practice. It is particularly advantageous that, because of the low viscosity of the basic monomer, the products have a relatively high content of this monomer.

In the context of the present invention, the substituents can have the following meaning:

An aliphatic radical (A) can be a straight-chain or branched hydrocarbon radical with 2 to 20, preferably 3 to 12, carbon atoms. The following aliphatic radicals may be mentioned as examples:

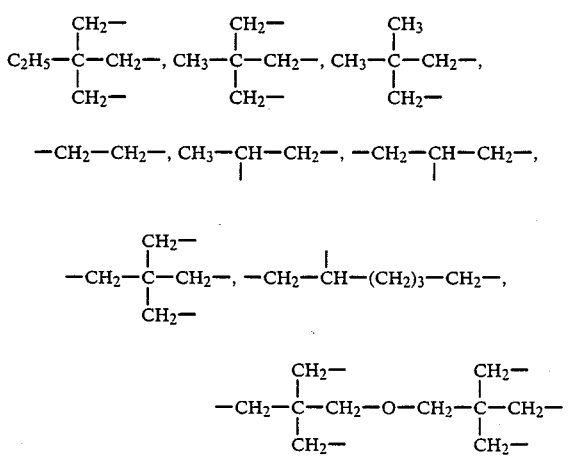

An aromatic radical (A) can be an aromatic hydrocarbon radical with 6 to 24, preferably 6 to 14, carbon atoms. The following aromatic radicals may be mentioned as examples:

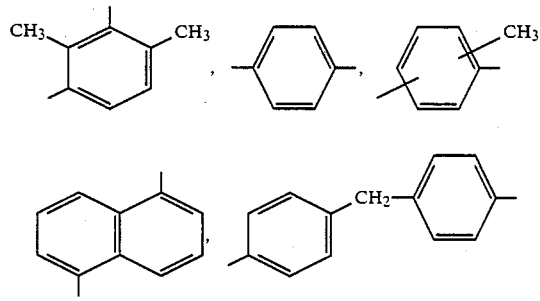

An araliphatic radical (A) can denote a hydrocarbon radical with a straight-chain or branched aliphatic and an aromatic part with 7 to 26 carbon atoms, the aromatic part preferably containing 6 to 12 and the aliphatic part preferably containing 1 to 14 carbon atoms. The following araliphatic radicals may be mentioned as examples:

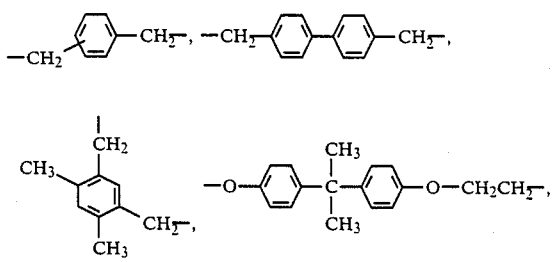

-continued

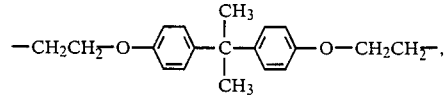

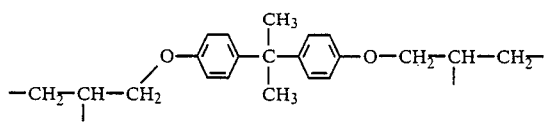

A cycloaliphatic radical (A) can be a cyclic hydrocarbon radical with 6 to 26 carbon atoms, preferably 6 to 14 carbon atoms. The following cycloaliphatic radicals may be mentioned as examples:

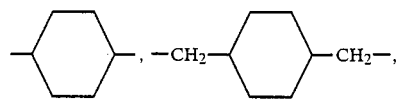

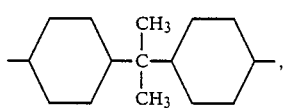

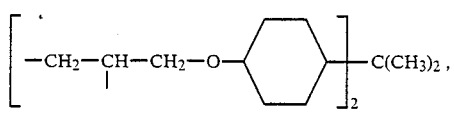

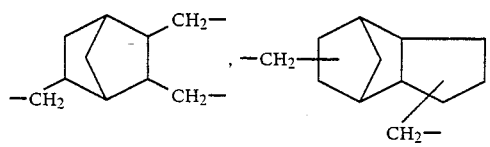

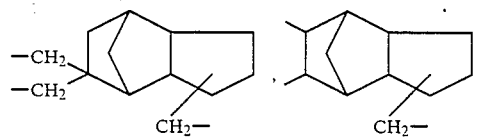

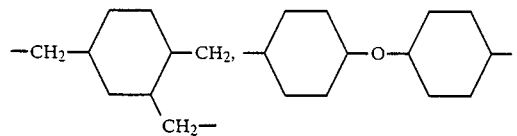

The radicals A can contain, preferably in the aliphatic or cycloaliphatic part, 1 or 2, preferably 1, oxygen atoms, so that, for example, aliphatic or cycloaliphatic ethers are present.

The following radicals A may be mentioned as particularly preferred: ethylene, propylene, 2,2-bismethylenebutan-1-yl, 2,2-bismethylene-propan-1-yl, 2,2-bis-methylene-propane-1,3-diyl, 1,1'-oxy-bis[(2,2-methylene)-propane-1,3-diyl], propane-1,2,3-triyl, 1,6-hexamethylene, 1,4-tetramethylene, 1,4-phenylene, xylylene, 1,4-cyclohexylene, 1,4-bismethylene-cyclohexane, 2,2-bis(1,4-phenylene)-propane, 3(4),8(9)-bismethylene-tricyclo[5.2.1.0$^{2.6}$]decane and its isomers and 4(5),9-bismethylene-3,8-dimethyltricyclo[5.2.1.0$^{2.6}$]decane.

The radicals 2,2-bismethylene-butan-1-yl, propane-1,2,3-triyl, 2,2-bismethylenepropane-1,3-diyl and 3(4),8(9)-bismethylene-tricyclo[5.2.1.0.$^{2.6}$]decane are preferred.

The following are mentioned as examples of groups X:

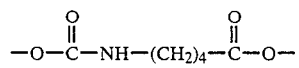

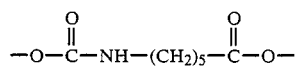

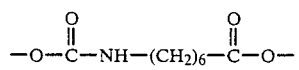

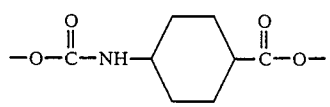

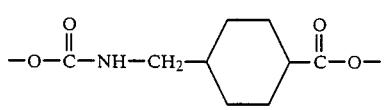

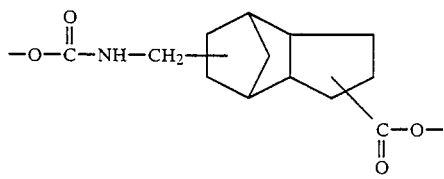

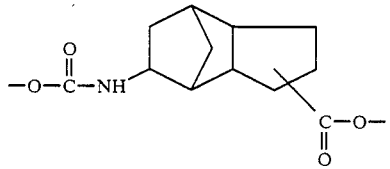

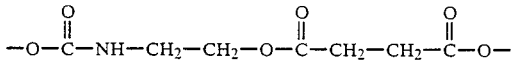

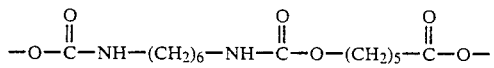

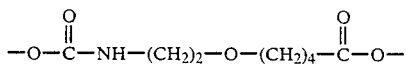

A divalent hydrocarbon radical (Z) can denote a straight-chain or branched aliphatic hydrocarbon with 3 to 15 carbon atoms, preferably 3 to 10 carbon atoms. The radical Z can optionally contain 1 to 3 oxygen bridges, preferably 1 or 2 oxygen bridges. It is also possible for the radical Z to be substituted by 1 to 4, preferably 1 or 2, (meth)-acrylate radicals. The following radicals may be mentioned as examples:

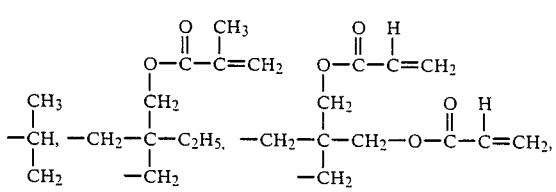

-continued

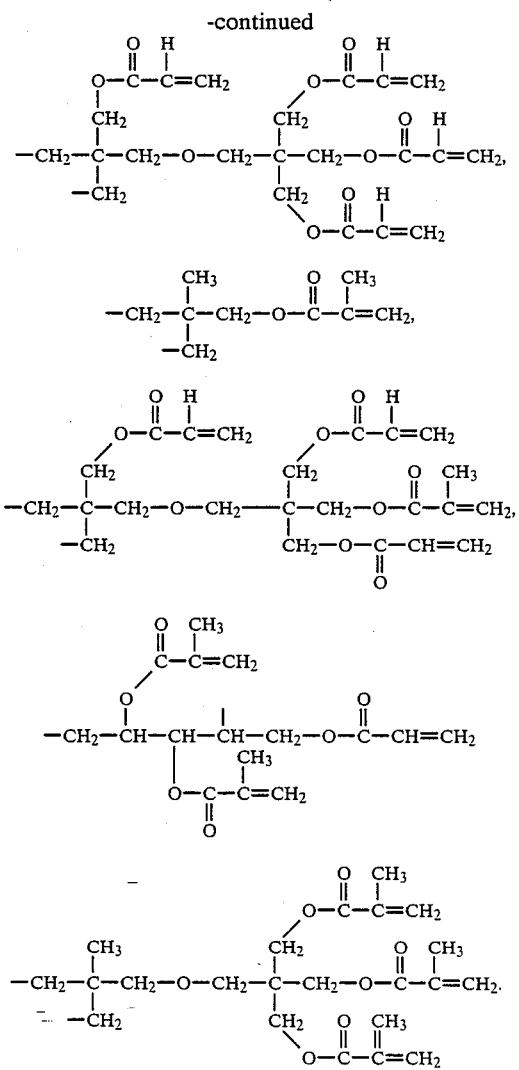

Preferred ester-urethane derivatives of (meth)-acrylic acid of the formula (I) are those in which
A is a straight-chain or branched aliphatic radical which has 3 to 12 carbon atoms and optionally contains 1 to 3 oxygen bridges, an aromatic radical with 6 to 14 carbon atoms, an araliphatic radical with 7 to 26 carbon atoms or a cycloaliphatic radical with 6 to 14 carbon atoms, r stands for the number of chains starting from A and denotes a number from 2 to 6,
$R^1$ and $R^2$ are identical and denote hydrogen or are different and denote hydrogen and methyl,
n denotes a number from 0 to 5 independently for each chain starting from A,
X stands for a group

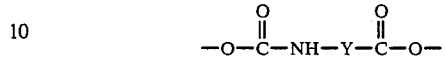

in which
Y denotes a divalent aliphatic radical with 2 to 10 carbon atoms,
Z denotes a divalent straight-chain or branched aliphatic hydrocarbon which has 3 to 10 carbon atoms and can optionally contain 1 or 2 oxygen bridges and can optionally be substituted by 1 or 2 (meth)-acrylate radicals and
$R^3$ denotes hydrogen or methyl independently for each chain starting from A.

Particularly preferred (meth)-acrylic acid derivatives containing urethane groups, of the formula (I), are those in which
A denotes the 2,2-bismethylene-butan-1-yl radical, propane-1,2,3-triyl radical, 2,2-bismethylenepropane-1,3-diyl radical or 3(4),8(9)-bismethylene-tricyclo[5.2.1.0$^{2.6}$]decane radical,
r denotes the number of chains starting from A and denotes the number 3 or 4,
$R^1$ and $R^2$ are identical and denote hydrogen or are different and denote hydrogen and methyl, n denotes a number from 0 to 5 independently for each chain starting from A,
X denotes the group

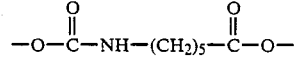

Z denotes a divalent straight-chain or branched aliphatic hydrocarbon radical which has 3 to 10 carbon atoms and can optionally contain 1 oxygen bridge and can optionally be substituted by 1 (meth)-acrylate radical and
$R^3$ denotes hydrogen or methyl independently for each chain starting from A.

The following ester-urethane derivatives of (meth)-acrylic acid may be mentioned as examples:

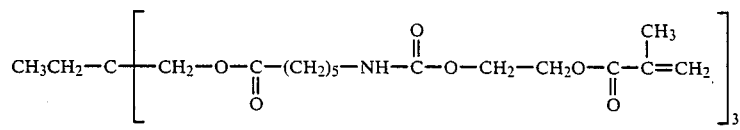

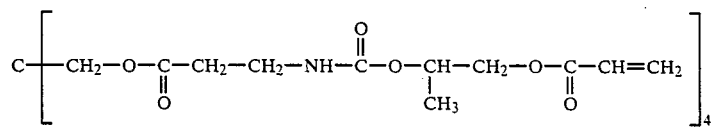

-continued
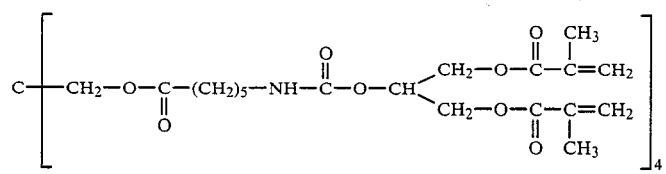
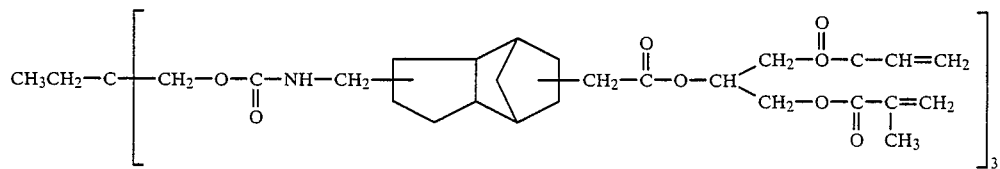
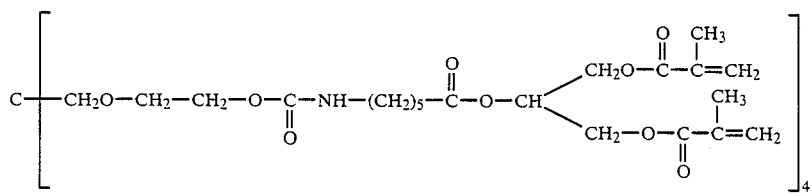
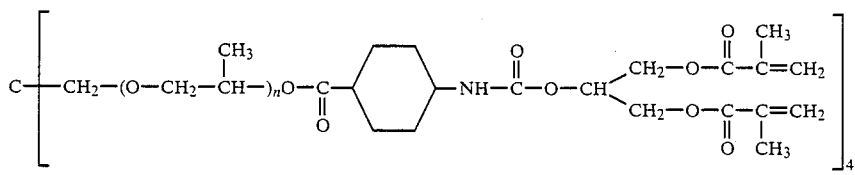
n = 1.225 (statistical mean value for 4 chains)
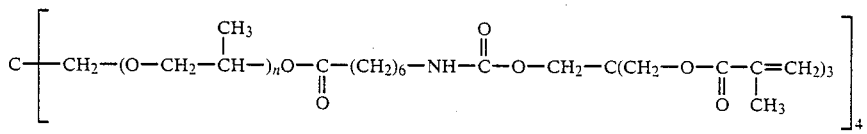
n = 1.225 (mean value)
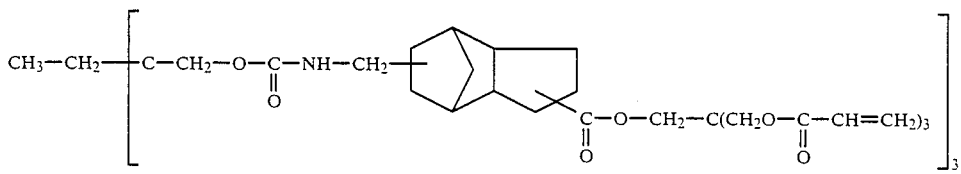
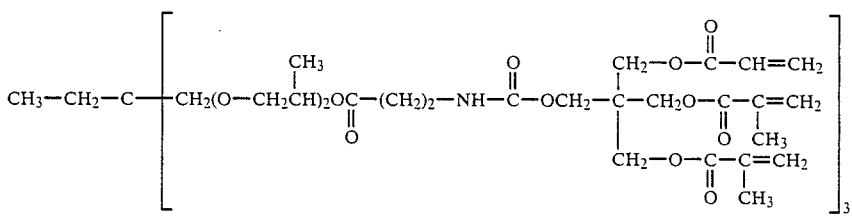

-continued
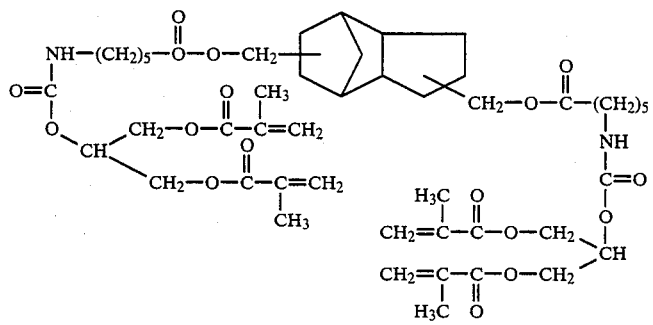
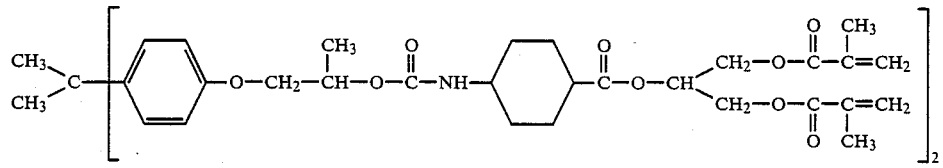
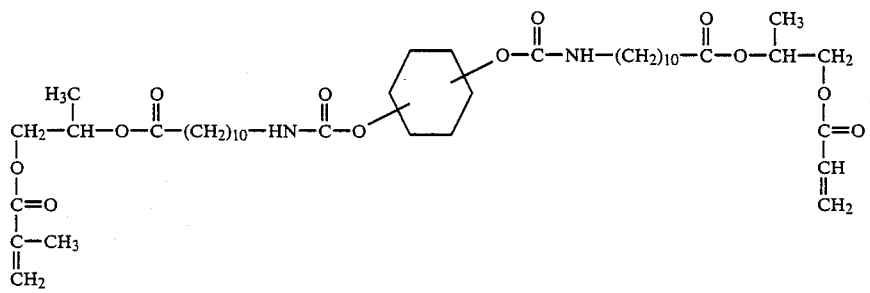
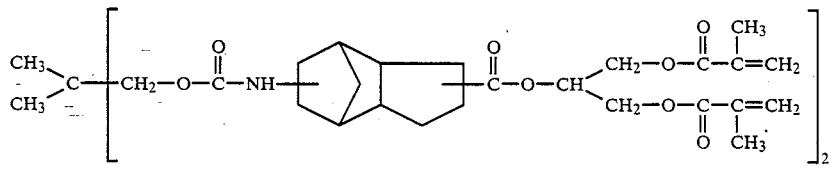
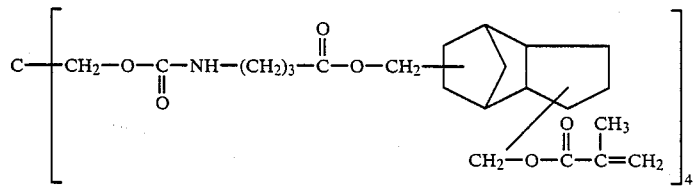
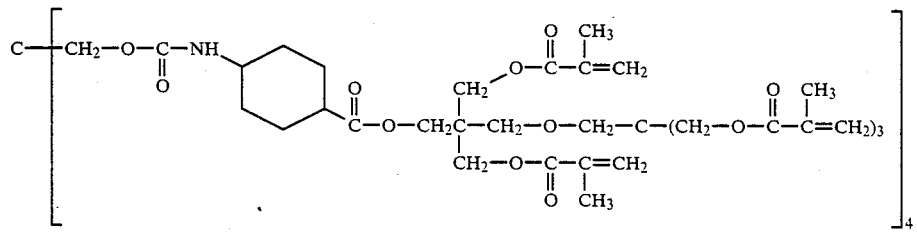
A process has also been found for the preparation of the ester-urethane derivatives, according to the invention, of (meth)-acrylic acid of the formula (I)
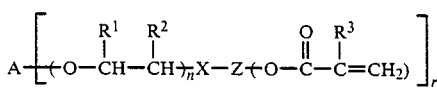
in which A is a straight-chain or branched aliphatic radical which has 2 to 20 carbon atoms and optionally contains 1 to 3 oxygen bridges, an aromataic radical with 6 to 24 carbon atoms, an araliphatic radical with 7 to 26 carbon atoms or a cycloaliphatic radical with 6 to 26 carbon atoms, r stands for the number of chains starting from A and denotes a number from 2 to 6, $R^1$ and $R^2$ are identical and denote hydrogen or are different and denote hydrogen and methyl, n denotes a number from 0 to 5 independently for each chain starting from A, X denotes the group

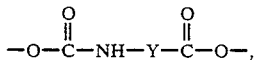

in which

Y denotes a divalent (cyclo)aliphatic radical which has 2 to 15 C atoms and optionally contains ester, ether or urethane groups, Z denotes a divalent straight-chain or branched aliphatic hydrocarbon radical which has 3 to 15 carbon atoms and can optionally contain 1 to 3 oxygen bridges and can optionally be substituted by 1 to 4 (meth)-acrylate radicals and $R^3$ denotes hydrogen or methyl independently for each chain starting from A, characterized in that the trialkylsilyl ether of a polyol of the formula (II)

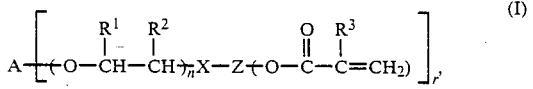

(I)

in which

A, $R^1$, $R^2$, n and r have the abovementioned meaning and $R^4$ to $R^6$ denote an alkyl radical with 1 to 4 carbon atoms, is reacted with an isocyanatocarboxylic acid chloride of the formula (III)

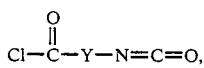

(III)

in which

Y has the abovementioned meaning, in a molar ratio of about 1:1, if appropriate in an inert solvent, and the isocyanato ester formed is then reacted with a (meth)acrylic acid hydroxyalkyl ester of the formula (IV)

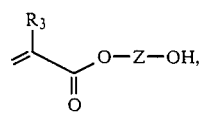

(IV)

in which $R_3$ and Z have the abovementioned meaning, in a molar ratio of OH groups to NCO groups of 0.98:1 to 1.05:1.

The polyols on which the trialkylsilyl ethers of the formula II are based are known per se (DE-A 2,931,925), or are commercially available and can be prepared, for example, by oxyalkylation of the known polyols of the formula A(OH)$_4$, for example 2,2-bishydroxymethylbutane, 2,2-bishydroxymethylpropane-1,3-diol, 3(4),8(9)-bishydroxymethyl-tricyclo[5.2.1.0$^{2.6}$]decane and the like. As a result of the preparation, the polyols can also be in the form of a product with a variable degree of oxyalkylation.

The silyl ethers II are availabale from the corresponding polyols and silylating reagents in a known manner, for example as in the derivatization of polyols for chromatographic purposes. Trialkylchlorosilanes, hexaalkyldisilazanes and the like, for example, are suitable for the silylation.

Isocyanatocarboxylic acid chlorides of the formula III are known and can be prepared by reaction of aminocarboxylic acids with phosgene (W. Mormann, S. Hoffmann, W. Hoffmann, Chemische Berichte 120, 285–290 (1987); and DE-A 2,120,090).

(Meth)-acrylic acid esters of the formula IV are known per se and can be obtained, for example by partial esterification of the corresponding polyols.

1st step

The reaction of the trialkylsilyl ether of the polyol II with the isocyanatocarboxylic acid chloride III is in general carried out in the temperature range from 80° to 150° C. without using solvents. If appropriate, solvents are used if the isocyanatocarboxylic acid chloride is a solid which is insoluble in the trialkylsilyl ether of the polyol. Solvents which contain no acid hydrogen, such as toluene, xylene, dioxane, acetonitrile, methyl isobutyl ketone and the like, are suitable.

The reactants is carried out under normal pressure or reduced pressure.

The reaction are reacted in equimolar amounts; a slight excess of III does no harm. The reaction is preferably initially carried out under normal pressure at 80°–150° C., whereupon some of the trialkylchlorosilane formed already distils off, for example if trimethylsilyl ethers and triethylsilyl ethers are used. After a reaction time of about 2 hours, the remainder of the trialkylchlorosilane is distilled off in vacuo in order to bring the reaction to completion. In the case of silyl ethers with propyl or butyl groups, a vacuum is applied from the beginning.

The conversion is virtually quantitative and can be monitored by gravimetric determination of the distillate. The products obtained by the 1st step of the reaction sequence process are isocyanato-(cyclo)alkyl esters of the polyols, as can be demonstrated by spectroscopic analysis.

2nd step:

The reaction to give the monomers is carried out in a second step which is characterized in that the isocyanate obtained in the first step is reacted with (meth)-acrylic acid hydroxyalkyl esters IV.

0.98 to 1.05 mol of IV per mol of isocyanate groups of the product obtained in the first step are used here.

Inert solvents are in general used for the second step of the process according to the invention. Examples which may be mentioned are acetone, chloroform, tetrahydrofuran, dioxane, methylene chloride, toluene and acetonitrile. Chloroform, toluene, acetonitrile and acetone are particularly preferred.

The second step of the process according to the invention is in general also carried out with exclusion of water. A maximum amount of water of less than 0.1% by weight, based on the total amount of the reactants, is particularly preferred.

Catalysts for the second step are in general metal salts of higher fatty acids. Preferred catalysts can be, for example, dibutyltin dilaurate, dibutyltin dimethoxide and tin(II) octoate. However, compounds with tertiary amino groups, such as triethylamine, pyridine, 2-methylpyridine, N,N-dimethylpiperazine and N,N-dimethyl-benzylamine can also be used as catalysts. It is also possible to use titanium compounds, such as tetrabutyl titanate.

The catalyst is in general used in an amount of 0.1 to 2.5% by weight, preferably 0.1 to 1.5% by weight, based on the total amount of the reactants.

In a preferred embodiment, the step of the process according to the invention is carried out in the presence of a polymerization inhibitor. Polymerization inhibitors are known per se (Ullmanns Enzyklopädie der techn. Chemie (Ullmann's Encyclopaedia of Industrial Chemistry), 4th edition, Verlag Chemie Weinheim, volume 8, pages 19–45). 2,6-Di-tert.-butyl-4-methylphenol, hydroquinone and hydroquinone monomethyl ether may be mentioned as examples.

It is also possible for oxygen, for example atmospheric oxygen, to be used as the polymerization inhibitor, this being passed into the reaction mixture.

The polymerization inhibitor is in general used in an amount of 0.01 to 1.0% by weight, preferably 0.1 to 0.2% by weight.

The second step of the process according to the invention is in general carried out in the temperature range from 0° to 100° C., preferably 30° to 70° C.

The process according to the invention is in general carried out under normal pressure. However, it is also possible for the process according to the invention to be carried out under reduced or increased pressure (for example in the pressure range from 0.1 to 10 bar).

The second step of the process according to the invention can be carried out, for example, as follows:

The (meth)-acrylic acid ester of the formula (IV) and if appropriate the polymerization inhibitor are dissolved in the inert solvent and added dropwise to the product from the first stept if appropriate dissolved, with stirring. The catalyst is at this step added to one of the two reactants.

0.98 to 1.05 mols of the hydroxyalkyl (meth)acrylate IV are preferably used per mol of NCO groups in the product of the first step.

The reaction is in general carried out until conversion is complete. When the reaction has ended, the reaction product is isolated by removal of the solvent. Previous filtration or purification with the aid of adsorbents, for example active charcoal, bleaching earth, silica gel or aluminum oxide, is possible.

The (meth)-acrylic acid derivatives obtained by the process according to the invention are monomer mixtures with a molecular weight distribution typical of the process.

It is also possible for the first and second stage of the abovementioned process to be interchanged in sequence. In this case, the corresponding trialkylsilyl ethers of the hydroxyalkyl (meth)acrylate must be reacted with the isocyanatocarboxylic acid chloride. The isocyanato-(meth)acrylate thereby obtained is then reacted in the second step with an amount of polyol corresponding to the NCO content.

However, the first variant of the process is preferred.

It is not necessary to separate the resulting reaction mixtures for the use according to the invention of the new ester-urethane (meth)acrylates in the dental field.

The mixtures themselves can advantageously be used as components of dental materials, for example dental filling materials.

The ester-urethane (meth)acrylates according to the invention can be used as monomers for dental materials. Examples of dental materials which may be mentioned are filling materials for teeth, coating agents for teeth and components for the production of false teeth, preferably false teeth of plastic. The dental materials can contain further additives, depending on the field of use.

For use as monomers for polymerizable dental filling compositions or coating agents in the dental field, the (meth)-acrylic acid derivatives according to the invention can be mixed with monomers which are known per se, for example in order to adjust the viscosity to suit the intended use. Viscosities in the range from 60 to 10,000 mPas are preferred here. This can be achieved by mixing, if appropriate, a comonomer of low viscosity as a reactive diluent or solvent with the monomers according to the invention. The compounds according to the invention are used in the mixture with the comonomers in an amount of about 40 to about 90% by weight, preferably 50 to 80% by weight. It is also preferable to use mixtures of different (meth)-acrylic acid derivatives according to the invention.

It is also possible to use monomer mixtures which contain several comonomers, in order to achieve the desired viscosity.

The following comonomers may be mentioned as examples: glycerol di(meth)acrylate, triethylene glycol di(meth)acrylate, tetraethylene glycol di(meth)acrylate, 1,12-dodecanediol di(meth)acrylate, 1,6-hexanediol di(meth)acrylate, diethylene glycol dimethacrylate, 2,2bis-[p-(2'-hydroxy-3'-methacryloyloxy propoxy)-phenyl]-propane, 2,2-bis-[p-(2'-methacryloyloxyethoxy)-phenyl]-propane, trimethlol-propane-tri-(meth)-acrylate and bis-(meth)acryloyloxyethoxymethyl-tricyclo-[5,2,1,0$^{2.6}$]-decane (DE-A 2,931,925 and DE-A 2,931,926).

Comonomers which have a boiling point above 100° C. under 13 mbar are particularly preferred.

The polyfunctional ester-urethane (meth)-acrylic acid esters according to the invention, if appropriate as a mixture with the comonomers mentioned, can be hardened to crosslinked polymers by methods which are known per se (Am. Chem. Soc., Symp. Ser. 212, 359–371 (1983)). A system of a peroxidic compound and a reducing agent, for example based on tertiary aromatic amines, is suitable for the so-called redox polymerization. Examples of peroxides are: dibenzoyl peroxide, dilauroyl peroxide and di-4-chlorobenzoyl peroxide.

Examples of tertiary aromatic amines which may be mentioned are N,N-dimenthyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline. the concentration of the peroxide and that of the amine are advantageously chosen so that they are 0.1 to 5% by weight, preferably 0.5 to 3% by weight, based on the monomer mixture. The peroxide- and amine-containing monomer mixtures are stored separately until used.

The monomers according to the invention can also be polymerized by irradiation with UV light or visible light (for example in the wavelength range from 230 to 650 nm). Examples of suitable initiators for the photoinitiated polymerization are benzil, benzil dimethyl ketal, benzoin monoalkyl ethers, benzophenone, p-methoxybenzophenone, fluorenone, thioxanthone, phenanthrenequinone and 2,3-bornanedione (camphorquinone), if appropriate in the presence of synergistic activators, such as N,N-dimethylaminoethyl methacrylate, triethanolamine and 4-N,N-dimethylaminobenzenesulphonic acid diallylamide. The photepolymerization procedure is described, for example, in DE-A 3,135,115.

In addition to the initiators described above, light stabilizers and stabilizers which are known per se for this intended use can be added to the (meth)-acrylic acid derivatives according to the invention.

Light stabilizers are described, for example, in (Gächter, Müller, Taschenbuch der Kunststoff-Additive (Handbook of Plastics Additives), 2nd edition, Carl Hanser Verlag). The following light stabilizers may be mentioned as examples: Cyasorp UV9 ®, Tinuvin P ®, Tinuvin 770 ® Tinuvin 622 ® and Tinuvin 765 ®.

Stabilizers are described, for example, in (Ullmanns Encyclopädie der technischen Chemie (Ullmann's Encyclopaedia of Industrial Chemistry), 4th edition, volume 8). The following stabilizers may be mentioned as examples: 2,6-di-tert,-butylphenol, 2,6-di-tert.-butyl-4-methylphenol, 2,6-di-octadecyl-4-methyl-phenol, 1,1'-methylene-bis(2-naphthol) and others.

The light stabilizers and the stabilizers can in each case be added in an amount of 0.01 to 0.5 part by weight per 100 parts by weight of the monomer mixture.

The monomer mixtures can be used as coating agents (dental lacquers) without the addition of fillers.

When used as dental filling compositions, fillers are in general added to the monomer mixtures obtained. Monomer mixtures which have a viscosity in the range from 60 to 10,000 mPas are particularly advantageous in order to be able to achieve a high degree of filling.

Inorganic fillers are preferably mixed with the (meth)-acrylic acid derivatives according to the invention. Examples which may be mentioned are rock crystal, cristobalite, quartz glass, highly disperse silicic acid, aluminum oxide and glass ceramics, for example glass ceramics containing lanthanum and zirconium (DE-A 2,347,591). The inorganic fillers are preferably pretreated with an adhesion promoter to improve adhesion to the polymer matrix of the polymethacrylate. The adhesion promotion can be achieved, for example, by treatment with organosilicon compounds (Progress in Organic Coatings 11, 197–308 (1983)). 3-Methacryloyloxypropyl-trimethoxysilane is preferably used. The fillers for the dental filling compositions according to the invention in general have an average particle diameter of 0.01 to 100 μm, preferably 0.03 to 50 μm and particularly preferably 0.03 to 5 μm. It may also be advantageous to add several fillers which have different particle diameters and/or different silane contents to one another side by side.

The filler content in the dental filling composition is in general 5 to 85% by weight, preferably 50 to 80% by weight.

For the preparation of the dental filling compositions, the components are mixed using commercially available kneading machines.

The content of the ester-urethane (meth)-acrylates according to the invention in the dental filling compositions is in general 5 to 50% by weight, based on the filling composition.

The ester-urethane derivatives, according to the invention, of (meth)-acrylic acid can also be used as components in the production of false teeth.

The monomers according to the invention are combined here with the constituents which are usually employed and are known per se. The monomers are preferably used as a mixture with alkyl methacrylates, such as methyl methacrylate. Bead polymers which are known per se can also additionally be added. Known inorganic and organic coloured pigments and clouding agents can be added to adjust the color of the teeth. It is also possible to use stabilizers and light stabilizers.

The teeth made of plastic are produced by free radical polymerization of the dental compositions, while shaping.

Processing is possible both by injection processes and by stamping processes, and is in general carried out by the customary methods for producing teeth based on poly(methylmethacrylate), for example by thermal polymerization using polymerization initiators which are known per se, for example those based on peroxides and azo compounds, such as dibenzoyl peroxide, dilauroyl peroxide, cyclohexylpercarbonate and azobisisobutyronitrile. Mixtures of polymerization initiators with different dissociation temperatures are also particularly suitable.

The dental materials prepared from the esterurethane (meth)acrylic acid esters according to the invention are distinguished by a high resistance towards mechanical stress and a high abrasion resistance. The abrasion resistance has been determined by the in vitro abrasion test described in the literature (J. Thiemann, W. Finger, B. Alker, M. Bock, IADR Paper No. 650 (1986)).

Preparation examples

EXAMPLE 1

Tetrakis-(trimethylsilyloxymethyl)methane 163.2 g (1.5 mols) of trimethylchlorosilane and 242.2 g (1.5 mols) of hexamethyldisilazane are added dropwise to a suspension of 136 g (1 mol) of pentaerythritol in 700 ml of toluene at room temperature. The mixture is stirred at room temperature for several hours. The product mixture is subjected to fractional distillation: Boiling point (0.3 mm Hg): 96°–98° C.

Yield: 331 g=78%.

Analysis by G.L.C.: at least 98%.

EXAMPLE 2

Preparation of the isocyanato ester 116.7 g (0.275 mol) of tetrakis-(trimethylsilyloxymethyl)methane and 192.8 g (1.099 mols) of isocyanatocaproyl chloride are stirred at 90° C. under 250 mbar for 7 hours. The mixture is then subsequently stirred at 110° C. under 250 mbar for a further 15 hours.

The trimethylchlorosilane formed in the reaction (110 g were isolated) is distilled into a cooled receiver and can be further used for the preparation of the silyl ether (Example 1).

The product which remains as the residue from the distillation is evacuated until it reaches constant weight. The product is a yellowish liquid.

Yield: 191 g

NCO content: 23.4%

IR (film on KBr) [$cm^{-1}$]: no absorption < 3000 (NH); 2250 (NCO), 1720

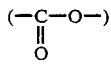

$^1$H-NMR (CDCl$_3$) [ppm]: 4.05 (2H)

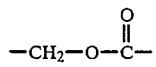

3.28 (2H, t)

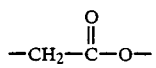

2.30 (2H, t) —CH$_2$NCO—1.60 and 1.35 (6H, m) —CH$_2$—.

EXAMPLE 3

Preparation of an ester-urethane methacrylate according to the invention 191 g of the polyisocyanate obtained in Example 2 are dissolved in 500 ml of chloroform. After addition of 0.26 g of 2,6-di-tert.-butyl-4-methyl-phenol and 0.3 g of tin(II) octoate, 241.4 g (1.06 mols) of glycerof dimethacrylate (mixture of the 1,2- and 1,3-diester) are added at room temperature.

The temperature is increased to 60° C. and is stirred at this temperature until conversion of the NCO group is complete. The solvent is then removed in vacuo.

IR spectrum (film on KBr) [cm$^{-1}$]: 3400 (N-H), 1720

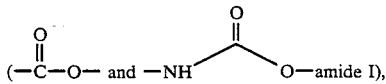

1600 (C═C), 1520 (amide II).

Yield: quantiatative.

Use examples

EXAMPLE 4

Preparation of a photoactivated coating agent (sealer)

0.5% by weight of N,N-diallyl-p-dimethylaminobenzenesulphonamide, 0.2% by weight of camphorquinone and 0.125% by weight of benzil dimethyl ketal are dissolved in a mixture of 40 parts by weight of neopentylglycol diacrylate and 60 parts by weight of monomer from Example 3.

When irradiated with a commercially available dental light source (Translux, Kulzer), the liquid hardens to a solid plastic.

Flexural strength (DIN 13 922) 85 MPa,
Flexuralmodulus (DIN 13 922) 1830 MPa,
Water absorption 1.7 mg/cm$^2$

EXAMPLE 5

Preparation of a photoactivated sealer 0.5% by weight of N,N-diallyl-p-dimethylaminobenzenesulphonamide, 0.2% by weight of camphorquinone and 0.125% by weight of benzil dimethyl ketal are dissolved in a mixture of 35 parts by weight of neopentylglycol dimethacrylate and 65 parts by weight of the monomer from Example 3.

The shaped article obtained after irradiation with a commercially available dental lamp (60 seconds, visible light) has the following properties:

| Flexural strength | 80 MPa |
|---|---|
| Flexural modulus | 1690 MPa |
| Water absorption | 2.0 mg/cm$^2$ |
| Abrasion test* | 103 ± 1% |

*based on the abrasion of a filling material (Estic microfill) used as a standard at 100%.

It is understood that the specification and examples are illustrative but not limitative of the present invention and that other embodiments within the spirit and scope of the invention will suggest themselves to those skilled in the art.

We claim:

1. A polyfunctional ester-urethane derivative of (meth)acrylic acid of the formula

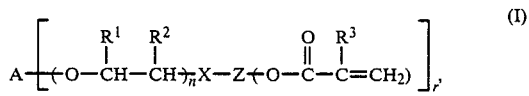

in which

A is a straight-chain or branched aliphatic radical which has 2 to 20 carbon atoms and optionally contains 1 to 3 oxygen bridges, an aromatic radical with 6 to 24 carbon atoms, an araliphatic radical with 7 to 26 carbon atoms or a cycloaliphatic radical with 6 to 26 carbon atoms, r dentotes the number of chains starting from A and denotes a number from 2 to 6, R$^1$ and R$^2$ are identical and denote hydrogen or are different and denote hydrogen and methyl, n denotes a number from 0 to 5 independently for each chain starting from A, X stands for the group

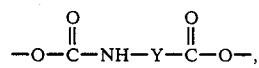

in which

Y denotes a divalent (cyclo)aliphatic radical which has 2 to 15 carbon atoms and optionally contains ester, ether or urethane groups, Z denotes a divalent straight-chain or branched aliphatic hydrocarbon radical which has 3 to 15 carbon atoms and can optionally contain 1 to 3 oxygen bridges and can optionally be substituted by 1 to 4 additional (meth)-acrylate radicals and R$^3$ denotes hydrogen or methyl independently for each chain starting from A.

2. A polyfunctional ester-urethane derivative of (meth)acrylic acid according to claim 1, wherein A is a straight-chain or branched aliphatic radical which has 3 to 12 carbon atoms and optionally contains 1 to 3 oxygen bridges, an aromatic radical with 6 to 14 carbon atoms, an araliphatic radical with 7 to 26 carbon atoms or a cycloaliphatic radical with 6 to 14 carbon atoms, r denotes the number of chains starting from A and denotes a number from 2 to 6, R$^1$ and R$^2$ are identical and denote hydrogen or are different and denote hydrogen and methyl, n denotes a number from 0 to 5 independently for each chain starting from A, X denotes the group

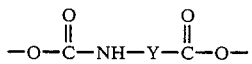

in which

Y denotes an alkylene radical with 2 to 10 carbon atoms,

Z denotes a divalent straight-chain or branched aliphatic hydrocarbon which has 3 to 10 carbon atoms and can optionally contain 1 or 2 oxygen bridges and can optionally be substituted by 1 or 2 (meth)acrylate radicals and $R^3$ denotes hydrogen or methyl independently for each chain starting from A.

3. A polyfunctional ester-urethane derivative of (meth)acrylic acid according to claim 1, wherein A denotes the 2,2-bismethylene-butan-1-yl radical, propane-1,2,3-triyl radical, 2,2-bismethylenepropane-1,3-diyl radical or 3(4), 8(9)-bismethylenetricyclo[5.2.1.0$^{2,6}$]decane radical, r denotes the number of chains starting from A and denotes the number 3 or 4, $R^1$ and $R^2$ are identical and denote hydrogen or are different and denote hydrogen and methyl, n denotes a number from 0 to 5 independently for each chain starting from A, X denotes the group

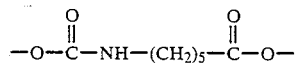

Z denotes a divalent straight-chain or branched aliphatic hydrocarbon radical which has 3 to 10 carbon atoms and can optinally contain 1 oxygen bridge and can optionally be substituted by 1 (meth)-acrylate radical and $R^3$ denotes hydrogen or methyl independently for each chain starting from A.

4. A process for the preparation of a polyfunctional ester-urethane derivative of (meth)-acrylic acid according to claim 1, which comprises reacting a trialkylsilyl ether of a polyol of the formula

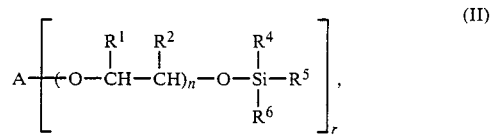

in which $R^4$ to $R^6$ stand for an alkyl radical with 1 to 4 carbon atoms, with an isocyanatocarboxylic acid chloride of the formula

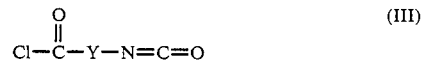

in a molar ratio of about 1:1 thereby to form an isocyanato ester, and reacting the isocyanato ester with a (meth)acrylic acid hydroxyalkyl ester of the formula

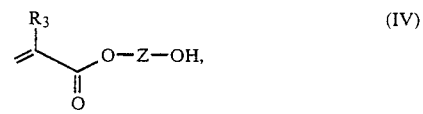

in a molar ratio of OH groups to NCO groups of about 0.98:1 to 1.05:1.

5. A process according to claim 4, wherein the reaction of the silyl ether with the isocyanato carboxylic acid chloride is carried out at a temperature from about 80° to 150° C.

6. A process according to claim 4, wherein the reaction of the isocyanato ester with the hydroxyl compound is carried out at a temperature from about 0° to 100° C.

7. A polymer of a polyfunctional ester-urethane derivative of (meth)-acrylic acid according to claim 1.

8. A dental filling, coating or tooth formed of a polymer according to claim 7.

9. A dental filling, coating or tooth according to claim 8, formed of a monomer according to claim 1 and a comonomer.

* * * * *